United States Patent [19]

Nagy et al.

[11] 4,120,657
[45] Oct. 17, 1978

[54] PROCESS OF AND EQUIPMENT FOR THE ANALYSIS OF LIQUID SAMPLES BY TITRATION

[75] Inventors: Geza Nagy, Debrecen; Erno Pungor, Budapest; Klara Toth, Budapest; Jeno Havas, Budapest; Zsofia Feher, Budapest, all of Hungary

[73] Assignee: EGYT Gyogyszervegyeszeti Gyar, Budapest, Hungary

[21] Appl. No.: 788,540

[22] Filed: Apr. 18, 1977

[30] Foreign Application Priority Data

Apr. 20, 1976 [HU] Hungary .............................. EE 2421

[51] Int. Cl.² ........................ B01K 3/00; G01N 31/16
[52] U.S. Cl. .................................. 23/230 R; 204/1 T; 204/195 T; 422/67; 422/75; 422/77; 422/100
[58] Field of Search ................. 23/253 R, 259, 230 R; 204/195 T, 1 T; 324/30 C

[56] References Cited

U.S. PATENT DOCUMENTS

| 3,195,982 | 7/1965 | Nicholson | 23/253 R |
| 3,870,466 | 3/1975 | Rellstar et al. | 23/253 X |

Primary Examiner—R.E. Serwin

[57] ABSTRACT

The invention relates to a process of and equipment for a selective, quick and accurate analysis of liquid samples. According to the process of the invention a liquid or a gas sample absorbed by a liquid is allowed to flow at a constant volume rate and overtitrated with an amount of a reagent adequate to the measurement in a definite time. Then the flow of the reagent is decreased to zero in a definite time, meanwhile continuously following, in a known way, the changes occurring in the reaction mixture. The determination of the concentration is carried out by comparing the time elapsed between the appearances of the two chemical equivalence points with calibration curves prepared with standard solutions, said time having a well defined functional relationship with the concentration of the sample.

The equipment according to the invention for carryinng out the process according to the invention contains an analysis channel in contact with a sample-storage tank or liquid storage tank or sampling device or liquid feeding device, said analysis channel comprising a gas-permeable membrane contacting a sample gas before the titration section if desired, said analysis channel being equipped with a pump, said analysis channel having a titration section comprising a small-volume flow-through homogenizing space and a reagent feeder or reagent generator device coupled to a programming unit and joining said channel before the said homogenizing space. For the measurement and recording of changes occurring in time, said analysis channel has, in its section between said homogenizing space and the suitably shaped effluent section, a detector section containing one or more detectors and a recording and/or indicator unit; if desired, said analysis channel has an electronic signal processing unit coupled to the recording and/or indicator unit and to the programming unit.

The accuracy of analyses carried out by the process and equipment according to the invention is identical with or higher than that of automatic titrators, and its velocity is identical with that of measurements carried out by flowthrough analysis channels, combining in this way all the advantages of both methods and measuring instruments.

9 Claims, 1 Drawing Figure

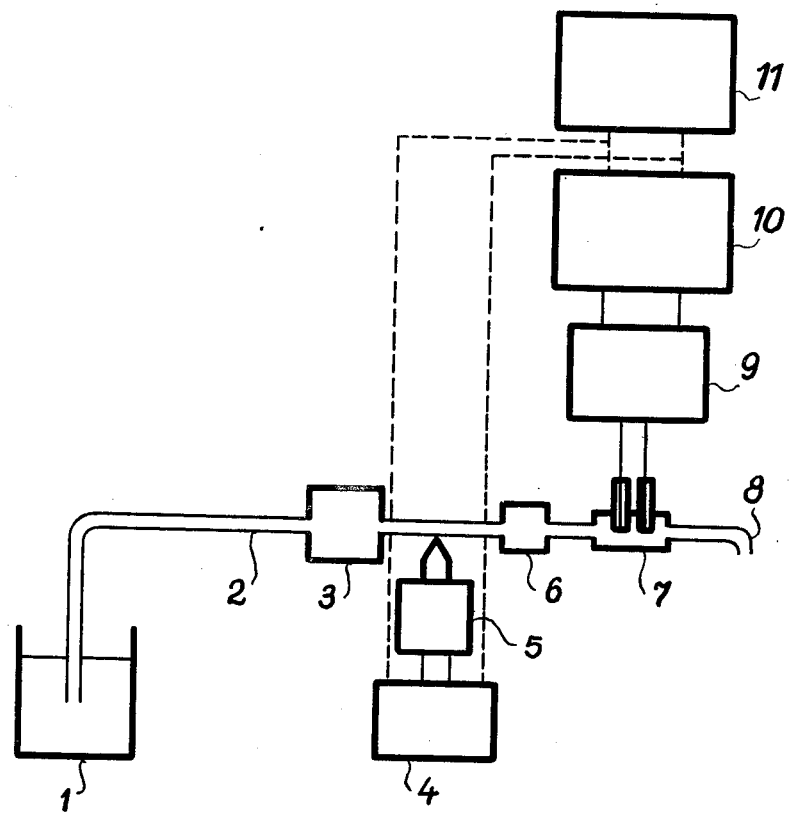

PROCESS OF AND EQUIPMENT FOR THE ANALYSIS OF LIQUID SAMPLES BY TITRATION

The invention relates to a process and equipment for the selective, quick and accurate analysis of liquid samples.

The number of chemical analyses to be carried out increases rapidly with the development of the chemical industry, environmental control, clinical diagnostics etc. This necessitates the development of automatic analyzer equipments.

The first automatic analyzers suitable for the determination of the concentration of sample solutions were automatic titrators carrying out accurately the work of the man performing the analysis. In a cycle automated to different degrees these titrators pass a known amount or volume of the sample to be measured into a previously washed titration vessel, then they add automatically an appropriate reagent from a burette to the sample and determine the amount of the reagent solution being chemically equivalent to the substance to be determined in the tested sample. Subsequently, the vessel is washed, the automatic burette is filled up again with the reagent solution, and the equipment is ready for a new analysis cycle (Phillips, J.P.: Automatic Titrators, Academic Press, New York - London, 1959). In these titrators various high-accuracy instrumental detection techniques are applied for the determination of the chemical equivalence point (Csanyi, L. - Farsang, Gy. - Szakacs,O. Instrumental analysis /in Hungarian/, Tankonyvkiado, Budapest, p.19). When approaching the equivalence point, a way of reagent addition is applied which makes possible the accurate observation of this point (see in the above cited book by Phillips). Accordingly, the analyses carried out by automatic titrators are highly accurate, and the manual methods applied earlier could be directly used in the atomic equipment. However, the mechanized titrator equipments are rather complex and the analysis with their use is cumbersome and unfavourably slow.

The application of the concept of "flowthrough analysis channels" denoted a qualitative improvement in the development of automatic equipments suitable for the measurement of the concentration of solutions. In this case the sample solutions and the calibrating standard solutions pass the analysis channel after each other at a constant volume velocity, separated from each other by an air bubble and by a washing liquid. At a certain point of the channel a reagent solution is added to the sample solution at a constant rate. The chemical reaction takes place in the channel in a longer or shorter time, then the reaction mixture enters the detector space where a continuously operated sensor detects the signal depending on the concentration of the sample. On comparing the signal measured in the sample solution with that obtained in the standard solutions, the measurement or determination of the concentration is possible (Bater, G.R.: Determination of pH. Wiley, New York, 1965; the above cited book by Csanyi et al.). Known automatic analyzer systems developed on the basis of the concept of flowthrough analysis channel are e.g. the Technicon Auto Analyzer (U.S. Pat. No. 3,484,170; Automation in Analytical Chemistry, Technicon Symposium, Brighton, 1967), or the BTL Analmatic and the Swedish AGA Autochemist equipments. By means of them the time required for analysis can be shortened to a great extent. It has been proved by the practice that analyzers carrying out determinations in the titration vessel in subsequent cycles are not competitive with equipments wherein the concept of flowthrough analysis channels is applied to serial routine measurements. At the same time the accuracy and reliability of measurements carried out with automatic equipments using a flow-through analysis channel are less favourable than those of measurements performed with titrators. This is due to the fact that an evaluation using the size of the signal level of the detector is affected by even small changes in the sensitivity of the detector and by smaller or greater interfering effects caused by the presence of other components in the sample solution to an extent much greater than that affecting an evaluation based on the end point of the titration.

The objective of the invention is the development of a measuring process and equipment combining the advantages of the concept of flowthrough channel and chemical analysis by titration i.e. wherein the rate of carrying out the analysis is identical with the rate of measurements carried out by the flowthrough analyzer channel and the accuracy is identical with that of automatic titrators or even exceeds it.

Up to the present, attempts of carrying out titrations in flowthrough system in automated operation did not give satisfactory results (Fleet, B.-Ho,A.Y.W.: Ion selective Electrodes, Ed. Pungor, E., Akademiai Kiado, Budapest, 1973, p. 17). This is due to two facts. On one hand, the technique applied for the preparation of the reagent, i.e. the gradient dilution, excludes the making of serial measurements (namely, repeated washings of vessel and accurate volume adjustments are required at the preparation of the reagent). On the other hand, the evaluation and the end point determination of the titration are inaccurate since the flow of the solution is slower along the walls of the tube than in the centre. Thus, the concentration of the reagent is changed to a certain degree, and it is difficult to state the real addition rate of the reagent in the observed end point. Accordingly, no process and equipment are known at present by means of which quick and accurate analyses could be carried out by the periodic titration of a sample solution continuously flowing in an analysis channel or of sample solutions flowing in a way separated from each other.

The invention is based on one hand on the recognition that the concentration of a flowing solution can be carried out very accurately by means of a programmed reagent administration provided a cyclic reagent administration programme is applied which secures that during a stage of the administration programme the reagent is present in an excess in comparison to the sample (overtitration). (The excess of the reagent relates to the occurrence of the chemical reaction serving as a basis of the determination.). On the other hand, we have recognized that on adequately choosing the reagent administration programme, the stoichiometric equivalence of the material flow of the flowing solution and of the material flow of the reagent (the equivalence point suitable for the determination of the concentration) can be determined easily.

The process of the invention consists essentially in administering to a liquid sample flowing at a constant volume rate one or several reagents corresponding to the nature of measurement for definite periods, preferably in a period of 30 seconds to 5 minutes, in increasing amounts, thus overtitrating the sample, then decreasing the added material flow of the reagent or reagents to zero, similarly in a definite period, meanwhile following, in a known way, the changes which take place in the reaction mixture, and taking the time elapsed between the occurrence of the two chemical equivalence points or an amount being in any functional connection with this time as a basis for the determination of the concentration. The unknown concentration is determined from the amount serving as a basis of the determination of concentration or from an adquate signal by comparison with standard solutions or by calculation.

Also gas samples can be analyzed by the process of the invention provided an absorbing liquid being in direct contact or through a membrane permeable to gases in an indirect contact with the gas is allowed to flow at a constant volume rate.

The equipment of the invention is essentially an analyzer channel equipped with a pump serving for keeping the liquid sample in flow, a section of the channel being constructed as a small-volume flow-through homogezining space. A reagent feeder combined with a programming unit joins the section before the homogenizing space, whereas the section after the homogenizing space serves as a detector space equipped with one or more detectors suitable for the measurement and recording of the changes occurring during the titration. The channel is fed from a sample store or sampling device, and the channel is ending in a drain formed expediently.

According to the invention the equipment can be formed also in a way that the section of the analyzer channel before the reagent feeder unit is shaped in a manner suitable for gas absorption. Gas absorption can be carried out preferably in a way that the absorbing liquid flowing in a flowthrough gas absorbing device comes into a direct contact with the gas or in a way that the concerned section of the analyzer channel is separated from rhe gas sample by a membrane permeable to gases.

In the course of the measurement the chemical reaction takes place, in the liquid flowing in the channel at a constant rate, between the liquid or gas sample and the reagent to an increasing extent, corresponding to the reagent addition starting from zero value and increasing in the programmed way. After attaining the chemical equivalence point between the material flow of the sample and that of the reagent, the reagent will be present more and more in an excess. Following the overtitration of a practical extent, the material flow of the reagent is decreased to zero according to a predetermined well defined program and the analysis is ended. If the same sample solution flow is present in the analysis channel, the analysis can be repeated or if a new sample solution is allowed to flow, a new measurement can be carried out by an adequate change of the reagent and of its feeding program.

Changes occurring as a result of the titration reaction during the cycles of reagent administration can be followed by means of the detector section or the detector system. Owing to the programmed feeding of the reagent, the material flow of a component of the sample and the material flow of the reagent twice attain the chemical equivalence point during one measurement. A well definable functional relationship exists between the time Q elapsed between the occurrence of the two chemical equivalence points and the concentration C of the component to be measured in the sample. In case of a reagent feeding starting from zero and changing according to a programme corresponding to an equilateral triangle shape $$Q = 2\tau - nkC \text{ ps}$$

wherein $\tau$ is the length of the increasing and decreasing periods of the material flow of the reagent (i.e. the length of the whole programme is $2\tau$), and $n$ and $k$ are constants depending on the stoichiometry of the titration reaction and on the slope of the time-schedule of the material flow of the reagent.

In this way, the concentration of the flowing solutions can be measured very accurately on the basis of a previous calibration with standard solutions or by means of calculation. Measurement according to the invention is in fact based on the determination of equivalence points of the titration which can be observed very accurately. Since the time elapsed between the occurrence of the two equivalence points or a quantity being in a given functional relationship serves as dependent variable for the calibration, the uncertainties of evaluation occurring in the measurements by titration carried out earlier in flowing solutions are eliminated by measurements performed according to the invention. The application of the concept of flowthrough analysis channels ensures a short analysis period. A particular advantage of the measurement process according to the invention is that accurate measurements are possible in a range between very broad concentration limits by adequate alterations in the reagent admistration program. In case of sample solutions containing several different compoments participating in the titration reaction there is also a possibility of determining the individual components in the presence of each other. Obviously this is possible when an adequate selective analytical reaction and/or detector or detector system is applied.

Thus, according to the invention one or more reagents appropriate to the measurement are added in a volume or concentration increasing for a predetermined time to a liquid sample flowing at a constant volume rate or to a gas sample absorbed by a liquid, the sample is overtitrated, then the added material flow of the reagent/reagents is decreased to zero in a definite period, meanwhile the changes occurring in time in the reaction mixture are continuously measured in a known way, and the time elapsed between the occurrence of the two chemical equivalence points or a quantity in a functional relationship with this time is taken as a basis for the determination of the concentration or concentrations of the sample, and lastly the concentration or concentrations of the emasured sample are determined from the obtained value or values by comparison with standard solutions or by calculation. The uniform distribution of the reaction and the accuracy of measurement are ensured by stirring.

IN THE DRAWING

The sole FIGURE is a diagrammatic layout of a preferred embodi-ent of equipment in accordance with the invention.

The equipment according to the invention consists of an analysis channel 2 which can be fed from a sample-storage or liquid storage tank 1 or from a sampling or liquid sampling device, said analysis channel comprsing before the titration section, if desired, a gas-permeable membrane being in contact with a gas sample, said analysis channel being equipped with a pump 3, said analysis channel having a titration section comprising a small-volume flowthrough homogenizing space 6, and a reagent feeder or reagent generator device 5 coupled to a programming unit 4 and joining the channel before the said homogenizing space, said analysis channel having, for the measurement and recording of changes occurring in time, in its section between the homogenizing space and the expediently shaped effluent section 8, a detector section comprising one or more known detectors 9 and a similarly known recording device 10.

By means of the equipment of the invention, measurement of concentration can be realized in an advantageous way. In this case a direct feedback is installed between the detector or detector system and the programming unit. Reagent feeding programmed according to the invention is carried out preferably by means of the programmable burette 5 coupled to the programming unit 4 according to the invention. This is suitable mainly for the programmed alterations of the volume rate of the administered reagent solution of small volume and high concentration. Similarly, the unit ensuring the programmed feeding according to the invention, the so-called programmed coulometric reagent generator unit can be constructed by coupling a current generator of programmable type to a function generator, applying a flowthrough coulometric generator cell corresponding to the coulometric technique and a pair of electrodes. The use of the programmed coulometric reagent generator unit is preferable for the preparation of reagents allowing a current efficiency of nearly 100% under the given conditions and at a maximum current density. It is expedient to transfer the reagent prepared by coulometry from the electrolyte by means of an adequately chosen electrolyte into the analysis channel with a solution flowing at a constant volume rate or to prepare it directly by means of a generator electrode located in the channel itself. Accordingly, the reagent feeder unit is constructed according to the invention either in a shape programmed by volume or in a shape where the concentration of the reagent is programmed.

The programme determining the flow in time of the reagent stream entering the flowthrough analysis channel corresponds suitably to a simple or complex function that can be described by curve having a maximum starting from zero material flow and returning again to zero.

On applying an isosceles triangle as reagent feeding program and when the tailing of the reagent solution during its flow is negligible in the analysis channel, then on recording the alterations in time of the signal indicated by the detector, two titration curves located symmetrically to each other are obtained due to a reagent feeding cycle. On the basis of the material balance, the relationship mentioned already above can be derived between the time O elapsed between the occurrence of the chemical equivalence points of the two titration curves which appear as the minor picture of each other and the concentration C of the sample solution. On the basis of this relationship or by a comparison with standard solutions the highly accurate titrimetric determination of the concentration of the flowing solution is ensured.

The length of the time elapsed between the appearance of the two equivalence points is described by a more complex relationship when also a tailing of the reagent during flow must be taken into account. In this case, on plotting the signal vs. time during a programme according to an isosceles triangle, the two titration curves of symmetric position do not appear. However, the concentration of the sample solution can be determined also in this case.

In certain cases e.g. when the titration is to be performed - with a high accuracy in a narrow concentration range, it is suitable to apply a reagent addition programme based on a non-isosceles triangle shape. In this case, the material flow of the reagent is adjusted preferably at the start of the programme suddenly to a given value, and the partial programme increasing and later decreasing with time linearly is started at this point or continued to this point. In this case, the material flow of the reagent is adjusted at the termination of the programme suddenly to zero value. In other cases, the determination of the equivalence points can be made simpler, corresponding to the characteristics of the applied detector, by employing a reagent feeding time-scheduled programme other than that based on an isosceles triangle.

The duration of the cycle of the material flow programme of the reagent exerts essentially a fundamental effect on the length of the time required by the measurement. However, the increase of the rate of analysis attainable by reducing the length of the cycles is limited by the fact that the reagent flow program may be distorted during the tailing occurring in the course of flow. The faster are the cycles the greater is the hazard of distortion. The analysis channel of the equipment constructed on the basis of the process according to the invention and operating according to the invention is a short tube section ensuring a linear flow, and thus the tailing in the direction of the reagent flow is minimal during the flow. The small volume of the applied homogenizing space of the invention causes only a tailing of minimum extent. Thus a very high rate of analysis (20 to 200 analyses per hour) can be attained.

In case of reagent feeding by programmed electrolysis or programmed coulometry, the homogenizing section or unit serves preferably also as a unit interrupting the galvanic contact, thus, it eliminates the effect of the electric field created by the generator electrodes on the operation of the detectors, too.

The detectors applied in the equipment according to the invention are in themselves known flowthrough spectroanalytical or electroanalytical detectors or the combinations of such detectors. In certain cases, aspects facilitating the processing of signals are followed by the construction of detectors e.g. development of difference signals by means of identical detectors located at certain distance from each other in the stream etc.

The equipment of the invention can be constructed also in a way that the signal is processed by an electronic signal processing and data processing unit 11 whose functions include the control of the programming unit, the processing of the signals measured by the detector/detectors and the processing and storage of the obtained data of concentrations.

The process and equipment of the invention are illustrated by the Examples given below.

EXAMPLE 1

Determination of the chloride concentration in tap water.

A solution of potassium nitrate is allowed to flow to tap water in a way to obtain in the formed sample solution a potassium nitrate concentration of $10^{-1}$ mol. This sample solution is then allowed to flow in the analysis channel 2 by means of liquid pump 3 at a constant volume rate of 5-10 ml/minute.

For the determination of the concentration of chloride ions an $Ag^+$ reagent is applied. In this case, the reagent is prepared by a programmed coulometric process using a rod-shaped silver metal anode in the generator cell 5.

The determination is based on the reaction:

$$Ag^+ + Cl^- \rightarrow AgCl$$

The reagent programme is chosen in a way to obtain at the maximum of reagent feeding (V = 5 ml/minute, $i_{max}$ = 16 mA, $C_{Cl}$ = $5.10^{-4}$ – $1.10^{-3}$ mol) an amount of silver about twice as great as the silver amount equivalent to the material flow of chloride ions calculated from the chloride ion content of the sample to be analyzed and from the flow rate of the sample.

The detector cell 7 contains an ion selective chloride electrode serving to follow the chloride concentration and a reference electrode of the second kind.

The results of measurements are evaluated as a function of the time elapsed between the appearances of the equivalence points on the basis of a comparison with values obtained by identical measurements in standard samples.

EXAMPLE 2

Determination of the contents of chloride and cyanide in an industrial sewage.

The determinations of concentration are based on the reactions:
a) $Ag^+ + Cl^- \rightarrow AgCl \downarrow$
b) $AG^+ + CN^- \rightarrow AgCN \downarrow$  $Ag^+ + 2 CN^- \rightarrow Ag(CN)_2^-$ Addition of the $Ag^+$ reagent for the determination of chloride ions is carried out in the way specified in Example 1, applying generation by coulometry.

The concentration of cyanide ions and chloride ions in the sample can be determined also by a single reagent feeding programme. However, the accuracy of the determination is signficantly increased if two programmes are applied for the determination of the concentration of these two ions. In this case, the maximum amount of produced silver is sufficient only for the titration (overtitration) of cyanide ions ($i_{max}$ = 2 mA). Accordingly, the concentration of cyanide ions can be determined in this step. In the second programme a reagent amount sufficient for the overtitration of both ions to be determined is generated ($i_{max}$ = 12.5 mA), thus, also the concentration of choride ions can be determined. The detector cell 7 is a potentiometric cell containing an ion selective indicator electrode in this case, too.

The concentration of chloride and cyanide ions is determined on the basis of curves of appearance time of equivalence point vs. concentration plotted with standard solutions. The standard deviation of chloride ion concentrations measured in the same sample solutions is 1-2%, that of measured cyanide ion concentrations is 3%.

EXAMPLE 3

Determination of the concentration of phenol in flowing sewages.

The determination is carried out on the basis of the reaction taking place between phenol and bromine.

The sample is allowed to flow in the analysis channel 2 at a rate of 5-10 ml/minute. Bromine is fed by means of coulometry. In this case, the reagent feeder 5 is a generator cell equipped with a platinum anode in which cell the electrochemical oxidation of bromine ions added in a concentration of 1 mol to the flowing sample solution proceeds. A generating current of 3-5 mA is applied. Detection is carried out by means of amperometry in the voltammetric detector cell 7 containing a platinum electrode.

The obtained results are evaluated on the basis of the time elapsed between the appearances of the equivalence points, by means of a calibration curve plotted according to the data obtained in measurements with standard phenol solutions in the concentration range of $1.10^{-5}$ to $10.10^{-5}$ mol.

The standard deviation of the results obtained is equivalent to 3-5%.

Although the invention is illustrated and described with reference to a plurality of preferred embodiments thereof, it is to be expressly understood that it is in no way limited to the disclosure of such a plurality of preferred embodiments, but is capable of numerous modifications within the scope of the appended claims.

What is claimed is:

1. A process for the selective analysis of flowing liquid samples, comprising flowing said liquid at a constant volume rate, feeding into the flowing liquid sample an amount of a reagent adequate to the measurement of the concentration of at least one constituent of the sample in a first period of time, and decreasing to zero the rate of flow of the reagent within a second predetermined period of time, during said first and second periods observing the changes occurring in the reaction mixture, and carrying out the determination of the concentration of said constituent of the liquid sample by comparing the time which elapses between the appearances of the two chemical equivalence points with calibration curves prepared with standard solutions, such elapsed time having a known functional relationship with the concentration of said constituent of the liquid sample.

2. A process as set forth in claim 1, comprising preparing an amount of the reagent fed into the liquid sample adequate to the measurement of the said constituent of the liquid sample.

3. A process as set forth in claim 1, comprising feeding a regularly increasing amount of the reagent into the flowing liquid sample in a period of from 30 seconds to 5 minutes.

4. A process as set forth in claim 1, comprising preparing a program for determining the rate of feeding of the reagent, said program corresponding to a function describable by a curve having a peak and starting from a liquid sample flow rate of zero and returning at the end of the second period to a liquid sample flow rate of zero.

5. Equipment for the selective analysis of flowing liquid samples, comprising a source of liquid sample, an analysis channel fed with said sample from said source, a pump interposed in the analysis channel, said analysis channel having a titration section comprising a small volume flowthrough homogenizing space, means for feeding a reagent into the analysis channel upstream of said homogenizing space, a programming unit, means coupling the reagent feeder to the programmable unit, the analysis channel having an effluent section, said analysis channel having means for measuring and recording changes in the flowing liquid sample between the said homogenizing space and the effluent section with respect to time, and a detector section containing a cell comprising a detector and an indicator unit.

6. Equipment as set forth in claim 5, further comprising a gas-permeable membrane disposed across the analysis channel in a location upstream of the titration section.

7. Equipment as set forth in claim 5, comprising an electronic signal processing unit operatively associated with said analysis channel, said signal processing unit being coupled to the indicator and to the programming unit.

8. Equipment as set forth in claim 5 wherein the reagent feeder is a programmable burette.

9. Equipment as set forth in claim 5, comprising a reagent generator, means for controlling the reagent generator by the programming unit, said reagent generator comprising a current generator coupled to a function generator, the function generator comprising a flowthrough coulometic generator cell and a pair of electrodes.

* * * * *